United States Patent
Auld et al.

(10) Patent No.: US 8,540,743 B2
(45) Date of Patent: Sep. 24, 2013

(54) HYDRAULIC VITRECTOMY PROBE

(75) Inventors: Jack Robert Auld, Laguna Niguel, CA (US); John Christopher Huculak, Mission Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 366 days.

(21) Appl. No.: 12/975,803

(22) Filed: Dec. 22, 2010

(65) Prior Publication Data

US 2012/0165724 A1 Jun. 28, 2012

(51) Int. Cl.
*A61B 17/32* (2006.01)

(52) U.S. Cl.
USPC .......................................................... 606/171

(58) Field of Classification Search
USPC ......... 606/166, 167, 169, 170, 171; 600/564, 600/565, 566, 567, 568
See application file for complete search history.

(56) References Cited

U.S. PATENT DOCUMENTS

| | | | | |
|---|---|---|---|---|
| 2,933,307 A * | 4/1960 | Williamson | ................... | 267/119 |
| 4,395,027 A * | 7/1983 | Nordmeyer | ...................... | 269/25 |
| 4,736,879 A * | 4/1988 | Yamada et al. | ................ | 227/130 |
| 4,818,190 A * | 4/1989 | Pelmulder et al. | ............ | 417/360 |
| 4,935,656 A * | 6/1990 | Kawamura | ................ | 310/156.08 |
| 5,113,808 A * | 5/1992 | Eickmann | ..................... | 123/55.2 |
| 5,344,395 A * | 9/1994 | Whalen et al. | ................... | 604/22 |
| 5,554,011 A | 9/1996 | Bales et al. | | |
| 5,564,436 A * | 10/1996 | Hakky et al. | ................... | 600/567 |
| 5,669,923 A | 9/1997 | Gordon | | |
| 5,871,462 A * | 2/1999 | Yoder et al. | ...................... | 604/22 |
| 6,220,271 B1 * | 4/2001 | Emmerich et al. | ............ | 137/113 |
| 6,224,617 B1 * | 5/2001 | Saadat et al. | ................... | 606/170 |
| 6,497,572 B2 * | 12/2002 | Hood et al. | ...................... | 433/81 |
| 6,638,235 B2 * | 10/2003 | Miller et al. | ................... | 600/566 |
| 6,689,072 B2 * | 2/2004 | Kaplan et al. | ................. | 600/567 |
| 6,742,236 B1 * | 6/2004 | Dion et al. | ....................... | 29/434 |
| 7,458,940 B2 * | 12/2008 | Miller | ........................... | 600/568 |
| 7,758,321 B2 * | 7/2010 | Fukano et al. | ................. | 417/384 |
| 8,328,831 B2 * | 12/2012 | Pein | .............................. | 606/167 |
| 2004/0133226 A1 * | 7/2004 | Buckman et al. | ............. | 606/167 |
| 2004/0267157 A1 * | 12/2004 | Miller et al. | ................... | 600/565 |
| 2005/0113715 A1 * | 5/2005 | Schwindt et al. | ............. | 600/566 |
| 2007/0185512 A1 | 8/2007 | Kirchhevel | | |
| 2008/0091225 A1 * | 4/2008 | Cole et al. | ...................... | 606/172 |
| 2009/0030436 A1 | 1/2009 | Charles | | |
| 2010/0209819 A1 * | 8/2010 | Fukuma et al. | ................ | 429/513 |
| 2012/0157906 A1 * | 6/2012 | Underwood et al. | ........... | 604/22 |

OTHER PUBLICATIONS

International Search Report and Written Opinion of the International Searching Authority, International Application No. PCT/2011/062773, dated Mar. 8, 2012, 10 pages.

\* cited by examiner

*Primary Examiner* — Ryan Severson
*Assistant Examiner* — Jonathan W Miles
(74) *Attorney, Agent, or Firm* — Darien Reddick

(57) ABSTRACT

Hydraulic vitrectomy probes and methods and systems associated therewith are discussed. Example hydraulic vitrectomy probes may include a pressure multiplier that is operable to output a hydraulic pressure at a multiple of a received pneumatic pressure. Because of the incompressible nature of liquid, hydraulic vitrectomy probes are, among other things, more responsive, may be operated at higher cutting rates, provide improved patient safety, and have a form factor (e.g., size and/or shape) that may be more easily maneuvered by a surgeon.

26 Claims, 5 Drawing Sheets

HYDRAULIC VITRECTOMY PROBE

TECHNICAL FIELD

The present disclosure relates to vitrectomy probes. Particularly, the present disclosure is directed to hydraulically actuated vitrectomy probes.

BACKGROUND

Vitrectomy probes are used during vitreoretinal surgery to remove ocular tissues, such as vitreous humor and membranes covering the retina. These probes may include a port for drawing in and dissecting tissues. Vitrectomy probes may be pneumatically or electrically powered.

SUMMARY

According to one aspect, the disclosure describes a hydraulic vitrectomy probe system. The system may include a pneumatic pressure source adapted to repeatedly cycle application of a pressurized gas, a hydraulically actuated vitrectomy probe, and a pressure multiplier coupled at a first portion to the pneumatic pressure source and at a second portion to the hydraulically actuated vitrectomy probe and adapted to convert a pneumatic pressure received from the pneumatic pressure source into a hydraulic pressure output to the hydraulically actuated vitrectomy probe. The pressure multiplier may include a first chamber, a first diaphragm housed in the first chamber, a second chamber, and a second diaphragm housed in the second chamber. The first diaphragm and the second diaphragm may be coupled to each other.

Another aspect encompasses a method of operating a hydraulically actuated vitrectomy probe. The method may include applying a pneumatic pressure from a pneumatic pressure source to a pressure multiplier, converting the pneumatic pressure into a hydraulic pressure with the pressure multiplier, and actuating a cutter of the vitrectomy probe with the hydraulic pressure supplied from the pressure multiplier to the hydraulically actuated vitrectomy.

A further aspect may include a hydraulic vitrectomy probe system including a pneumatic pressure source adapted to produce a pulsed pneumatic pressure by repeatedly cycling application of a pressurized gas, a hydraulic vitrectomy probe adapted to receive a pulsed hydraulic pressure, and a pressure multiplier in fluid communication with the pneumatic pressure source and the hydraulic vitrectomy probe. The pressure multiplier may be adapted to receive the pulsed pneumatic pressure and in fluid communication with the hydraulic vitrectomy probe transmit the pulsed hydraulic pressure to the hydraulic vitrectomy probe. The pressure multiplier may include a housing, a first chamber defined by a first portion of the housing, a second chamber defined by a second portion of the housing, a first diaphragm disposed in the first chamber, the first diaphragm having a surface in contact with the pressurized gas, and a second diaphragm disposed in the second chamber, the second diaphragm having a surface in contact with hydraulic fluid used to transmit the pulsed hydraulic pressure to the hydraulic vitrectomy probe. The first diaphragm may be coupled to the second diaphragm to form an operational assembly. The operational assembly may be adapted to convert the received pulsed pneumatic pressure into the pulsed hydraulic pressure.

The various aspects may include one or more of the following features. A first chamber of a pressure multiplier may be fluidly coupled to a pneumatic pressure source. A second chamber of the pressure multiplier may be fluidly coupled to a hydraulically actuated vitrectomy probe. The pressure multiplier may be coupled to a pneumatic pressure source via a conduit. The conduit may be flexible tubing. The pressure multiplier may be directly coupled to the pneumatic pressure source. The pressure multiplier may be integrated into the pneumatic pressure source. The pneumatic pressure source may form a part of an ophthalmic surgical console. A surface area of the first diaphragm in contact with a pressurized gas supplied by the pneumatic pressure source may be larger than a surface area of the second diaphragm in contact with a hydraulic fluid. The hydraulic vitrectomy probe may be coupled to the pressure multiplier via a conduit. The conduit may be flexible tubing. The hydraulic vitrectomy probe may be a single-action hydraulic vitrectomy probe. The hydraulic vitrectomy probe may be a dual-action probe.

A first pressure multiplier and a second pressure multiplier may be included. The second pressure multiplier may be fluidly coupled to the pneumatic pressure source at a first portion of the second pressure multiplier and the hydraulic vitrectomy probe at a second portion of the pressure multiplier. The first pressure multiplier may be adapted to supply hydraulic pressure to the hydraulic vitrectomy probe to actuate a cutter of the hydraulically actuated vitrectomy probe in a first direction. The second pressure multiplier may be adapted to supply hydraulic pressure to the hydraulic vitrectomy probe to actuate the cutter of the hydraulically actuated vitrectomy probe in a second direction, opposite the first direction.

The various aspects may also include one or more of the following features. Applying a pneumatic pressure from a pneumatic pressure source to a pressure multiplier may include supplying a pulsed pneumatic pressure to the pressure multiplier. Applying a pneumatic pressure from a pneumatic pressure source to a pressure multiplier may include applying the pneumatic pressure from the pneumatic pressure source that forms a part of an ophthalmic surgical console. Converting the pneumatic pressure into a hydraulic pressure with the pressure multiplier may include receiving the pneumatic pressure into a pneumatic portion of the pressure multiplier against a first diaphragm contained within the pneumatic portion and in fluid contact with a gas transmitting the pneumatic pressure. The first diaphragm may be coupled to a second diaphragm disposed in a hydraulic portion of the pressure multiplier. Converting the pneumatic pressure into a hydraulic pressure with the pressure multiplier may also include displacing the first diaphragm and the second diaphragm with the pneumatic pressure and displacing hydraulic fluid in contact with the second diaphragm to form the hydraulic pressure. Displacing the first diaphragm and the second diaphragm with the pneumatic pressure may include displacing the first diaphragm having a surface area in contact with the gas larger than a surface area of the second diaphragm in contact with the hydraulic fluid. Actuating a cutter of the vitrectomy probe with the hydraulic pressure supplied from the pressure multiplier to the hydraulically actuated vitrectomy may include cycling the cutter of the vitrectomy probe at a rate of in the range of one to 20,000 cycles per minute.

The various aspects may also include one or more of the following features. A first diaphragm and a second diaphragm of a pressure multiplier may include retaining features formed along peripheral edges thereof, and wherein the retaining features are received into respective recesses formed in a housing of the pressure multiplier. The operational assembly may include a spacer disposed between the first diaphragm and the second diaphragm. The spacer may be adapted to transmit a movement of one of the first diaphragm or the second diaphragm to the other of the first diaphragm or the second diaphragm. A surface area of the first diaphragm in contact with the pressurized gas may be larger than an area of the second diaphragm in contact with the hydraulic fluid. The pneumatic pressure source may be fluidly coupled to the pressure multiplier by flexible tubing. The hydraulic vitrectomy probe may be fluidly coupled to the pressure multiplier by flexible tubing. The pressure multiplier may be directly coupled to the pneumatic pressure source.

DETAILED DISCLOSURE

Figure 1:
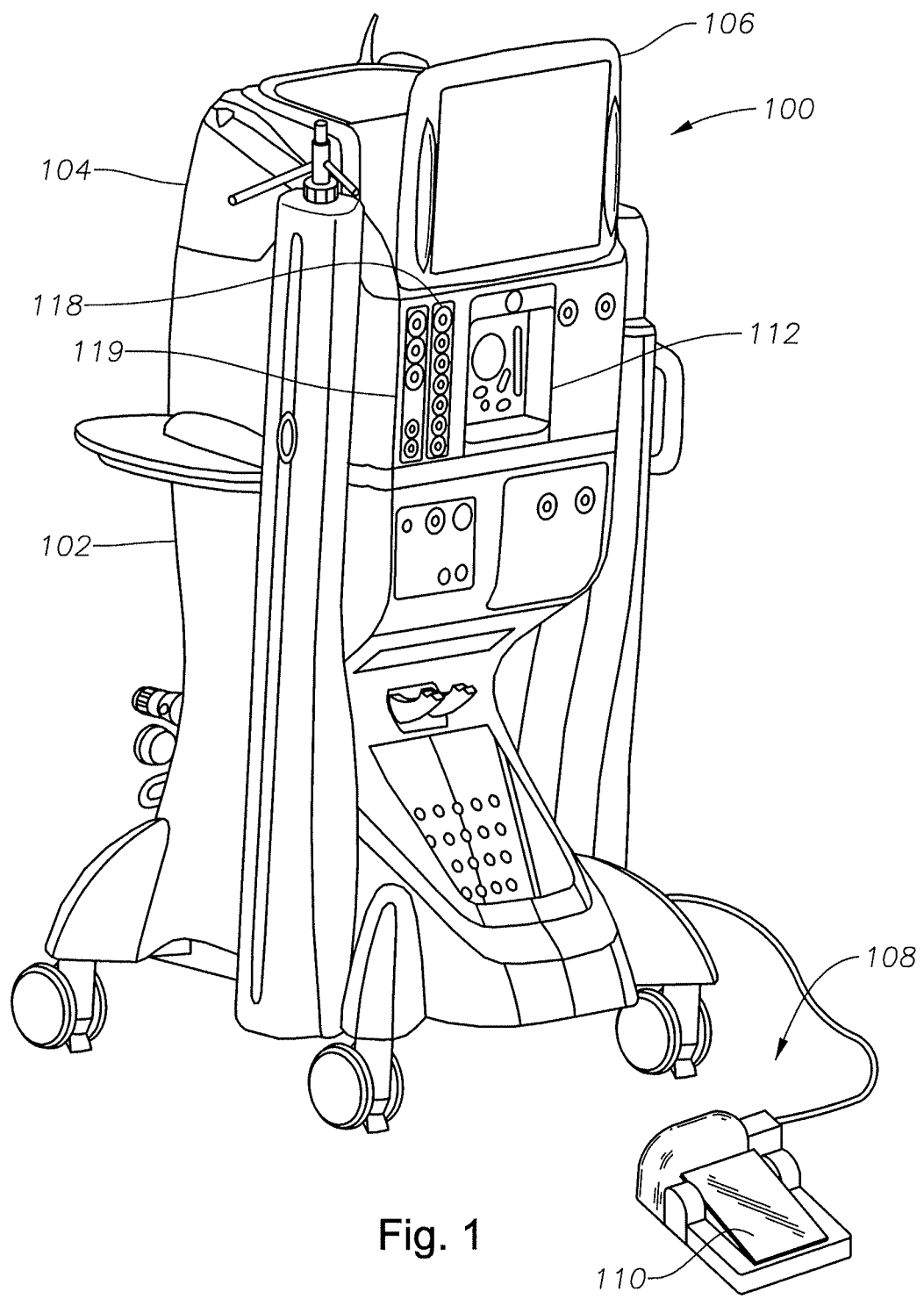
FIG. 1 shows an example surgical console that may be used with a hydraulic vitrectomy probe.

The present disclosure describes hydraulically-actuated vitrectomy probes (interchangeably referred to as "hydraulic vitrectomy probes"). Example hydraulic vitrectomy probes utilize a liquid, such a liquid readily available in a surgical environment. Example liquids include saline, BSS® ("Balanced Salt Solution" produced by Alcon Laboratories, Inc., of 6201 South Freeway, Fort Worth, Tex. 76134-2099), sterile water, silicon, and Perflouon® liquid, also produced by Alcon Laboratories, Inc. Other liquids may also be used.

Hydraulic vitrectomy probes offer numerous advantages, including improved response times, higher cutting speeds, increased duty cycles, and higher operating pressures. In some instances, hydraulic vitrectomy probes may have response times of three milliseconds at 5,000 cycles per minute and pressures of 30 psi. For example, the incompressible nature of liquids and the significantly higher wave propagation speed in liquids, as opposed to gases, provide for improved response time. Wave propagation in liquids is a function of the speed of sound, which is significantly higher than the speed of wave propagation in gases. Consequently, cutting speeds may be increased and a wider range of duty cycles may be available as a result of the reduced response time. Further, in some instances, response times may be less than one millisecond.

Other advantages include the ability to control operational aspects of the vitrectomy probe. For example, as a result of the incompressible nature of a hydraulic liquid, an opening size of the vitrectomy probe's aperture may be controlled. That is, the maximum opening size of the vitrectomy probe's aperture may be varied during a surgical procedure with the use of feedback control. Feedback control may be accomplished by, for example, sensing an amount of movement of the hydraulic liquid and directly correlating that movement to the opening size of the vitrectomy probe's aperture. In some instances, movement of the liquid may be accomplished by sensing an amount of movement of a diaphragm or piston used to displace the liquid. In some instances, movement of the diaphragm may be measured by capacitive distance measurement, inductive sensing, optical sensing, or with laser position transducers. However, other methods and systems may be used, and the examples listed above are provided merely as examples. Position feedback control, such as by sensing movement of the liquid, may also provide for duty cycle control. Duty cycle is the amount of time that a vitrectomy cutter port is open as a percentage of the total time of a cut cycle.

The correlation between movement of the hydraulic liquid and the vitrectomy probe's cutter combined with the ability to sense the movement of the hydraulic liquid also enables the probe's cutter position to be monitored. A monitoring scheme may be implemented in some instances to provide a warning, such as when a probe's cutter may be functioning improperly or contrary to an expected mode.

Additionally, hydraulic vitrectomy probes may be operated at higher fluid pressures, reducing a displaced volume of fluid compared, for example, to pneumatic vitrectomy probes. For example, hydraulic operating pressure from a few hundred to a thousand psi or more may be utilized in hydraulic vitrectomy probes. Consequently, hydraulic vitrectomy probes may have reduced sizes, smaller drive lines (e.g., conduits used to fluidly communicate hydraulic pressure to the vitrectomy probe), console-regulated position control (such as to control a size of the port of the vitrectomy probe), and reduced pressurized gas consumption. For example, a hydraulic vitrectomy probe may have a reduced diameter or otherwise have a reduced cross-section. Thus, in some implementations, a hydraulic vitrectomy probe may have a "pencil" diameter. Decreased probe sizes may provide for improved handling and control during a surgical procedure because of the physical space limitations around the eye experienced during ocular procedures. Smaller sized drive lines may provide improved clinical benefit to the surgeon. For example, smaller sized drive lines may have a smaller physical package, greater flexibility, and provide for a greater range of motion. Additionally, for vitrectomy probes utilizing a return spring, such as in a single-action vitrectomy probe, the spring may have a higher spring constant. A higher spring constant in combination with higher fluid pressures may result in vitrectomy probe with an increased cutting rate. Further, hydraulic vitrectomy probes may displace a lower volume of fluid and, because vitrectomy probes may be operated hat higher pressures, may more easily overcome internal probe friction within the surgical system.

Still further, hydraulic vitrectomy probes offer increased safety benefits. For example, compressed gas is eliminated from the hydraulic vitrectomy probe, thereby eliminating the risk of compressed gas escaping into a patient's eye. Additionally, redundant seals presently used to prevent compressed gas within pneumatic vitrectomy probes from escaping into the eye may be eliminated. Similarly, hydraulic vitrectomy probes may also be electrically isolated, further reducing the risk of harm to a patient as well as the surgeon.

Hydraulic vitrectomy probes may be primed immediately preceding a surgical procedure, such as in the operating room, as opposed to priming the probes during manufacturing. Also, priming of the hydraulic vitrectomy probes may be easily incorporated into current common priming sequences, making introduction and acceptance of the probes into medical practice comfortable for practitioners. Hydraulic vitrectomy probes may also be sterilized using current sterilization practices. For example, in some implementations, hydraulic vitrectomy probes may be sterilized with ethylene oxide ("EtO"). Additionally, hydraulic vitrectomy probes may be disposable after a single use, eliminating the need to sterilize the probes between treatments, further enhancing safety and reducing costs.

An additional benefit of hydraulic vitrectomy probes according to some implementations is that the hydraulic probes may be incorporated with existing pneumatic equipment with little, if any, modification. For example, some hydraulic vitrectomy probes may be coupled to existing surgical consoles used to supply compressed gas. The operational system architecture for hydraulic vitrectomy probes, e.g., dual-action and single-action probes, is also flexible. For example, a drive diaphragm or piston for driving hydraulic fluid may be completely contained within a consumable or a surgical console.

In some instances, a hydraulic vitrectomy probe may be used in combination with a surgical console, such surgical console 100 shown in FIG. 1. In some instance, the surgical console 100 may be a Constellation® Vision System produced by Alcon Laboratories, Inc., of 6201 South Freeway, Fort Worth, Tex. 76134-2099. However, hydraulic vitrectomy probes may be used in combination with other surgical consoles.

The console 100 may include a housing 102 with a controller 104 and an associated display screen 106 operable to show, for example, data relating to system operation and performance during a vitreoretinal surgical procedure. The console 100 may also include a number of systems that are used together to perform vitreoretinal surgical procedures. For example, the systems may include a footswitch system 108 including, for example, a footswitch 110, a fluidics system 112, and a pneumatics system 118. The pneumatics system 118 may be operable to supply power to and control a vitrectomy probe. For example, the pneumatics system 118 may be operable to repeatedly cycle application of a pressurized gas. In some instances, the pneumatic system 118 may be operable to cycle pressurized gas at rates within the range of one cycle per minute to 20,000 cycles per minute. In some implementations, the cycled gas may be applied at, for example, at different pressures, different rates, and different duty cycles. A vitrectomy probe may be interfaced with the console 100 via the pneumatics system 118 via panel 119 to control actuation of the cutter The fluidics system 112 may be operable to provide a vacuum to the vitrectomy probe, such as to aspirate materials during a surgical procedure. To optimize performance of the different systems during surgery, their operating parameters may be varied according to, for example, the particular procedure being performed, the different stages of the procedure, the surgeon's personal preferences, whether the procedure is being performed in the anterior or posterior portion of the patient's eye, and so on.

The different systems in console 100 may include control circuits for the operation and control of the various functions and operations performed by the console 100, such operations of a vitrectomy probe. The controller 104 may be operable to govern the interaction and relationship between the different systems to properly perform a vitreoretinal surgical procedure. To do this, the controller 104 may include one or more processors, one or more memory devices, and may be configured or programmed to control operations of the console 100, for example, based upon pre-established programs or sequences.

As shown in FIG. 1, the display screen 106 for viewing and access by a user rests on the housing 102. An input device permits a user to control images on the display and to make selections to control or modify the preprogrammed relationships between different systems. In some instances, the input device may be a touch screen device responsive to selections made directly on the screen 106.

Figure 2:
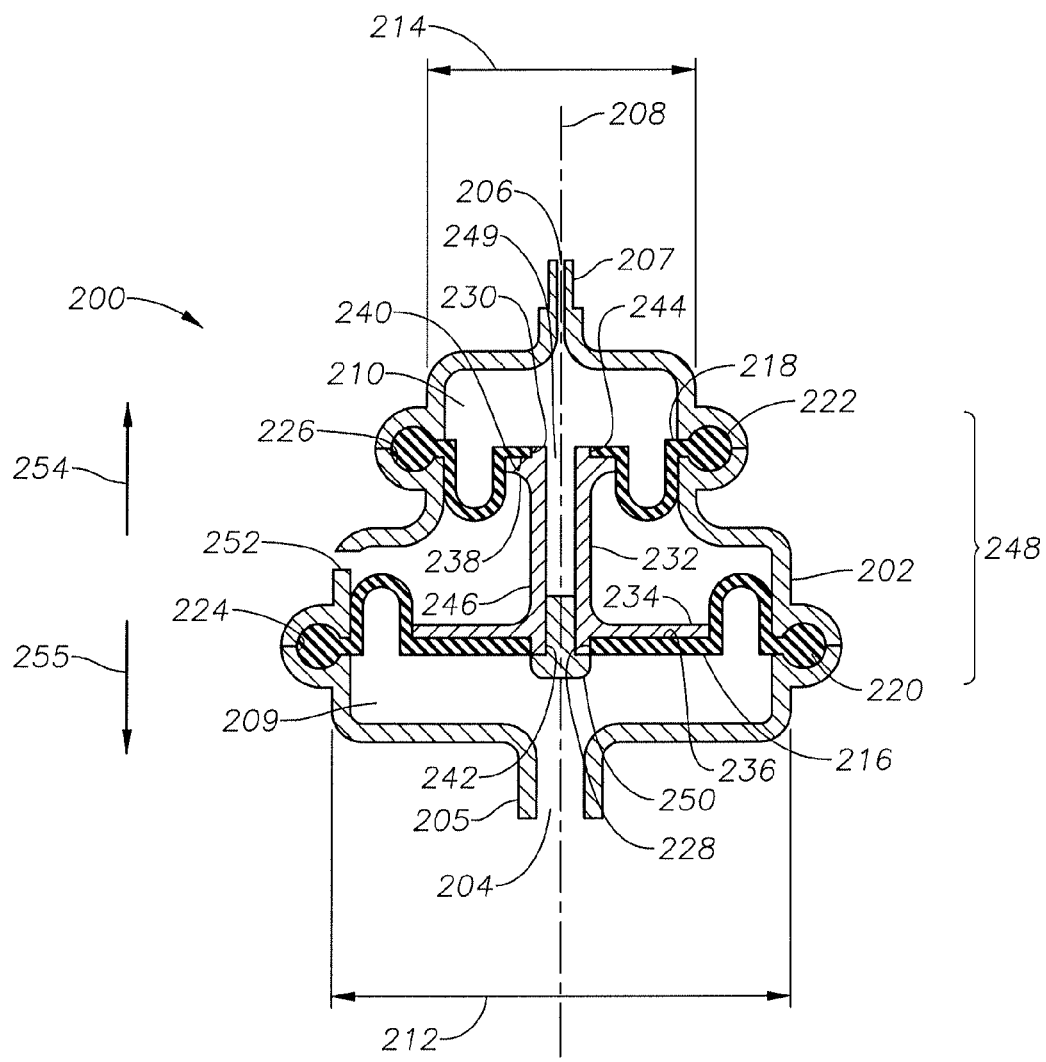
FIG. 2 is a cross-sectional view of an example pressure multiplier.

FIG. 2 shows a longitudinal cross-section of a pressure multiplier 200. The pressure multiplier 200 may coupled to a pneumatic system of a surgical console, such as the pneumatic system of the console 100. A hydraulic vitrectomy probe, such as the example hydraulic vitrectomy probes 300 and 400, shown in FIGS. 3 and 4, respectively (discussed in more detail below), may also be coupled to the pressure multiplier 200.

Referring again to FIG. 2, the pressure multiplier 200 may include a housing 202 having a first opening 204, a second opening 206, and a longitudinal axis 208. The housing 202 may include lips 205 and 207, circumscribing the first opening 204 and the second opening 206, respectively. The lips 205 and 207 may be used to attach a conduit, such as flexible tubing, to the pressure multiplier 200.

The example pressure multiplier 200 has a circular cross-sectional shape transverse to the longitudinal axis 208. However, other implementations may have different shapes. For example, in some instances, the housing 202 may have an elliptical, rectangular, square, or any other transverse cross-sectional shape. Thus, the example pressure multiplier 200 is provided merely as an example and is not intended to be limiting.

The housing 202 may form a first chamber 209 and a second chamber 210. As shown, the first chamber 209 may have a larger outer dimension 212 (e.g., diameter) than an outer dimension 214 (e.g., diameter) of the second chamber 210. A first diaphragm 216 may be disposed in the first chamber 208, and a second diaphragm 218 may be disposed in the second chamber 210. The first diaphragm 216 and the second diaphragm 218 may include retaining features 220 and 222, respectively. The retaining features 220, 222 may be accepted into retaining receptacles 224 and 226, respectively. The retaining features 220, 222 and the retaining receptacles 224, 226 may cooperate to form a seal. In some instances, the seals may be air-tight and/or liquid-tight. The first diaphragm 216 and the second diaphragm 218 may also include central openings 228, 230.

The first diaphragm 216 and the second diaphragm 218 may be joined by a spacer 232. The spacer 232 may include a first flange 234 that engages an interior surface 236 of the first diaphragm 216 and a second flange 238 that engages an interior surface 240 of the second diaphragm 218. In some instances, the spacer 232 may include lips 242, 244. The lips 242, 244 may be received into the central openings 228, 230, respectively. Interfaces between the central openings 228, 230 and the lips 242, 244 may form seals. In some instances, the seals may be air-tight and/or liquid-tight. In some instances, an adhesive may be used to secure the first flange 234 and the second flange 238 to the interior surfaces 236, 240, respectively, and, optionally, to surfaces forming the openings 228, 230. The first diaphragm 216, the second diaphragm 218, and the spacer 232 may form an operational assembly 248.

The spacer 232 may also include a central portion 246 that forms a central passageway 249. The central passage 248 may provide fluid communication between the first chamber 209 and the second chamber 210. In some instances, the central passage 249 may be used to introduce hydraulic fluid into the second chamber 210 and a hydraulic vitrectomy probe, thereby priming the vitrectomy probe. An example method of priming a hydraulic vitrectomy probe is described in more detail below. A plug 250 may be disposed in the central passage 249 to isolate the first chamber 209 from the second chamber 210.

The coupling of the spacer 232 with the first diaphragm 216 and the second diaphragm 218 enables the first diaphragm 216 and the second diaphragm 218 to operate in unison. Consequently, when one of the first diaphragm 216 or the second diaphragm 218 is displaced, the other of the first diaphragm 216 or the second diaphragm 218 is displaced in response. The displacement of the first diaphragm 216 and the second diaphragm 218 may occur substantially in unison. A port 252 may be formed in the housing 202 between the first diaphragm 216 and the second diaphragm 218. The port 252 may be operable to allow air to move into and out of the housing 202, equalizing pressure between the first and second diaphragms 216, 218, and, thereby, allowing the first and second diaphragms 216, 218 to move freely.

In an example implementation, the pressure multiplier 200 may be coupled to a pneumatic system, and the pneumatic system may communicate pressurized gas to the first chamber 209 of the pressure multiplier 200 through the first opening 204. In some instances, a conduit, such as flexible tubing, may be attached to the lip 205 and communicate the pressurized gas to the first chamber 216. Hydraulic fluid may be contained within the second chamber 210. Hydraulic pressure may be communicated from the second chamber to a hydraulic vitrectomy probe, such as the hydraulic vitrectomy probe 300 and/or 400, shown in FIGS. 3 and 4, respectively.

Pneumatic pressure introduced into the pressure multiplier 200 by pressurized gas via the first opening 204 acts upon the first diaphragm 216 to impart a force thereto. The applied force may cause the operational assembly 248 to be displaced in the direction of arrow 254. Consequently, hydraulic fluid contained within the second chamber 210 is displaced by movement of the operational assembly 254. Release of the pneumatic pressure causes the operational assembly 248 to move in the direction of arrow 255, for example, because of the biasing characteristics of the first and second diaphragms 216, 218.

The example pressure multiplier 200 may be operable to multiply a pneumatic pressure incident on the first diaphragm 216 and apply the multiplied pressure to the hydraulic fluid by the second diaphragm 218. For example, with the pressurized gas, having a pressure $P_1$, is in contact with an area, $A_1$, of the first diaphragm 216, the resultant pressure, $P_2$, applied to the hydraulic fluid in contact with an area, $A_2$, of the second diaphragm 218, is:

$$P_2=(A_1/A_2) \cdot P_1$$

Thus, for example, where the area of the first diaphragm 216 is twice the area of the second diaphragm 218, the pressure applied to the hydraulic fluid is two-times the pressure imparted by the pneumatic fluid. However, the pressure increase produced by the pressure multiplier may any desired amount. For example, the ratio of the area of the diaphragm in contact with the pneumatic pressure (interchangeably referred to as "the pneumatic portion diaphragm") to the area of the diaphragm in contact with the hydraulic liquid (interchangeably referred to as "the hydraulic portion diaphragm") may be selected to produce any desired pressure increase. For example, a fluid multiplier may be sized to produce an increase in pressure of a few hundred to a few thousand psi. Further, in some instances, the second opening 206 may be made smaller than the first opening 204. Thus, a conduit (e.g., flexible tubing) extending from the second opening 206 to a hydraulic vitrectomy probe may have a smaller cross-sectional shape (e.g., a smaller diameter). Thus, this conduit may be more easily maneuvered and articulated during a surgical procedure.

The increase in pressure produced by the pressure multiplier results in the need for a smaller diaphragm or other pressure-responsive device in the vitrectomy probe to actuate the probe a desired amount. Consequently, the probe diameter may be made smaller, e.g., having a smaller cross-sectional shape, enabling a surgeon to more easily manipulate the probe as well as provide more space around the eye in which to articulate the probe.

Figure 3:
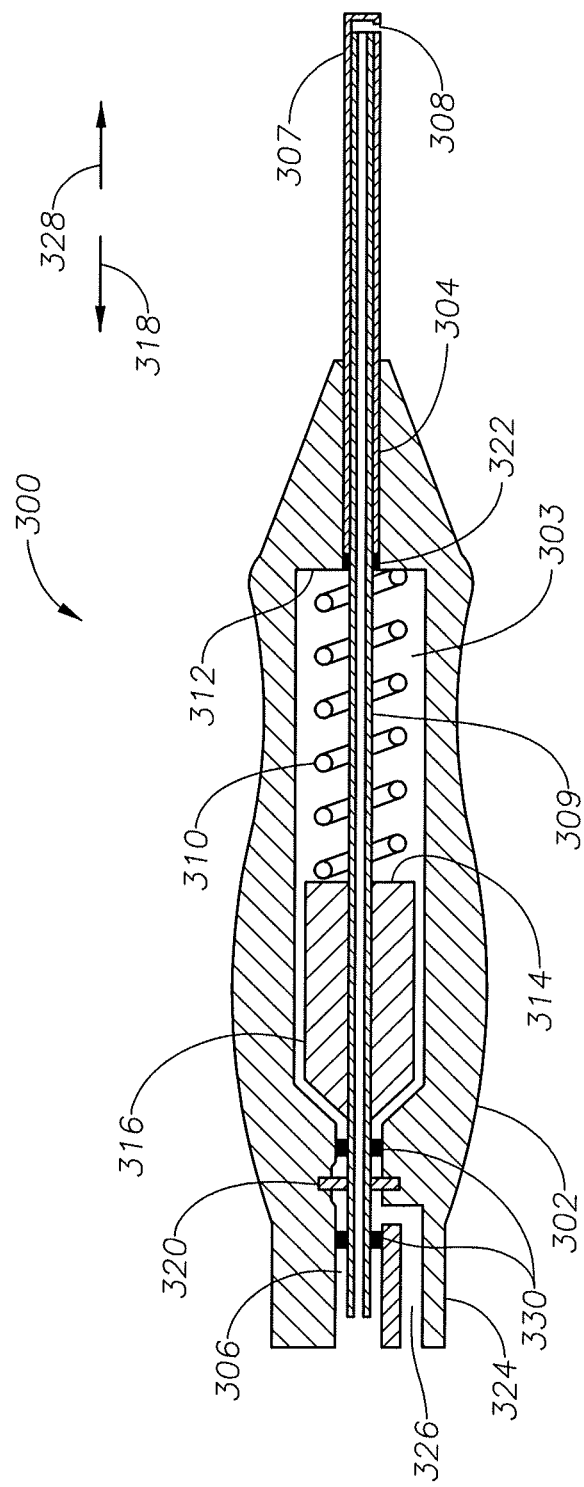
FIG. 3 is a cross-sectional view of an example single-action hydraulic vitrectomy probe.

A pressure multiplier, such as the example pressure multiplier 200, may be fluidly coupled to a hydraulic vitrectomy probe, such as a single-action or dual-action vitrectomy probe. FIG. 3 shows an example single-action vitrectomy probe 300. The probe 300 includes a housing 302 forming a central chamber 303, a first passage 304, and a second passage 306. An outer sleeve 307 having a port 308 may be fixedly attached to the housing 302 in the first passage 304. A cutter 309 extends through the second passage 306, the central chamber 303, and the outer sleeve 307. The cutter 309 may be hollow to allow aspiration of tissue, fluid, and other materials during operation of the probe 300.

A spring 310 is housed in the central chamber 303 and engages an interior wall 312 of the housing 302 and a surface 314 of a spring mount 316 attached to the cutter 309. The spring 310 biases the cutter 309 in a direction of arrow 318. The probe 300 also includes a diaphragm 320 coupled to the cutter 309 and the housing 302. A sealing member 322 may also be included between the cutter 309 and an interior surface of the first passage 304. Sealing members 330 may also be included. A conduit may be attached to the probe 300 at a connecting portion 324 of the housing 302. The connecting portion 324 may define at least a portion of a chamber 326.

Hydraulic fluid contained within the chamber 326 may act on the diaphragm 320, causing diaphragm 320 and cutter 309 to displace in the direction of arrow 328, and compressing spring 310. When hydraulic pressure is released, the spring 310 returns the cutter 309 and diaphragm 320 to an initial position. As hydraulic pressure is cycled, the hydraulic pressure and spring 310 cooperate to reciprocate the cutter 309. As a result, the cutter 309 is made to reciprocate within the outer sleeve 307 to perform a cutting action. Tissue entering port 308 may be cut by the reciprocating cutter 309, and the severed tissue may be aspirated through the cutter 309. In some instances, the stroke of the cutter 309 may be approximately 1 mm or less. However, in other instances, the stroke may be larger. That is, the stroke of cutter 309 may be selected to be any desired length. While FIG. 3 shows one example single-action hydraulic vitrectomy probe, other types of single-action vitrectomy probes are also within the scope of the disclosure.

Figure 4:
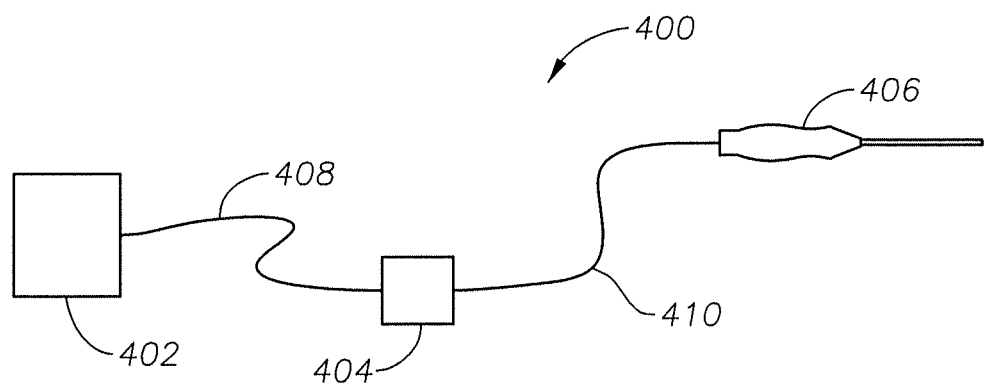
FIG. 4 is a schematic view of an example hydraulic vitrectomy probe system, such as for a single-action hydraulic vitrectomy probe.

An example hydraulic vitrectomy probe system 400 is shown in FIG. 4. The system 400 may include a pneumatic system 402, a pressure multiplier 404, and a vitrectomy probe 406. The example vitrectomy probe 406 may be similar to the vitrectomy probe 300, described above. A first conduit 408, such as flexible tubing, may extend between the pneumatic system 402 may and the pressure multiplier 404. A second conduit 410, which may also be flexible tubing, extends between the pressure multiplier 404 and the hydraulic vitrectomy probe 406.

In operation, the pneumatic system 402 may pulse pneumatic pressure through the first conduit and into a pneumatic portion of the pressure multiplier 404. In a manner similar to the operation of the pressure multiplier 200, described above, the pressure from the pneumatic pressure may be applied to a hydraulic portion of the pressure multiplier 404 and magnified an amount according to the geometry of the pressure multiplier 404, such as the ratio of the area of the pneumatic portion diaphragm to the area of the hydraulic portion diaphragm, as discussed above with respect to FIG. 2.

While the pressure multiplier 404 is shown coupled to the pneumatic system 402 with the first conduit 408, in other instances, the pressure multiplier 404 may be coupled directly to the pneumatic system 402, or, in still other instances, integrated into the pressure system 402. Locating the pressure multiplier 402 closer to the pneumatic system 402, such as with a shorter conduit or by directly mounting or integrating the pressure multiplier 404, thereby eliminating the conduit altogether, reduces the size of the pneumatic reservoir that must be displaced to actuate the pressure multiplier 404 and the vitrectomy probe 406. Thus, with a smaller pneumatic reservoir, there is less compression of the pneumatic fluid and, therefore, a quicker response of the vitrectomy probe.

Figure 5:
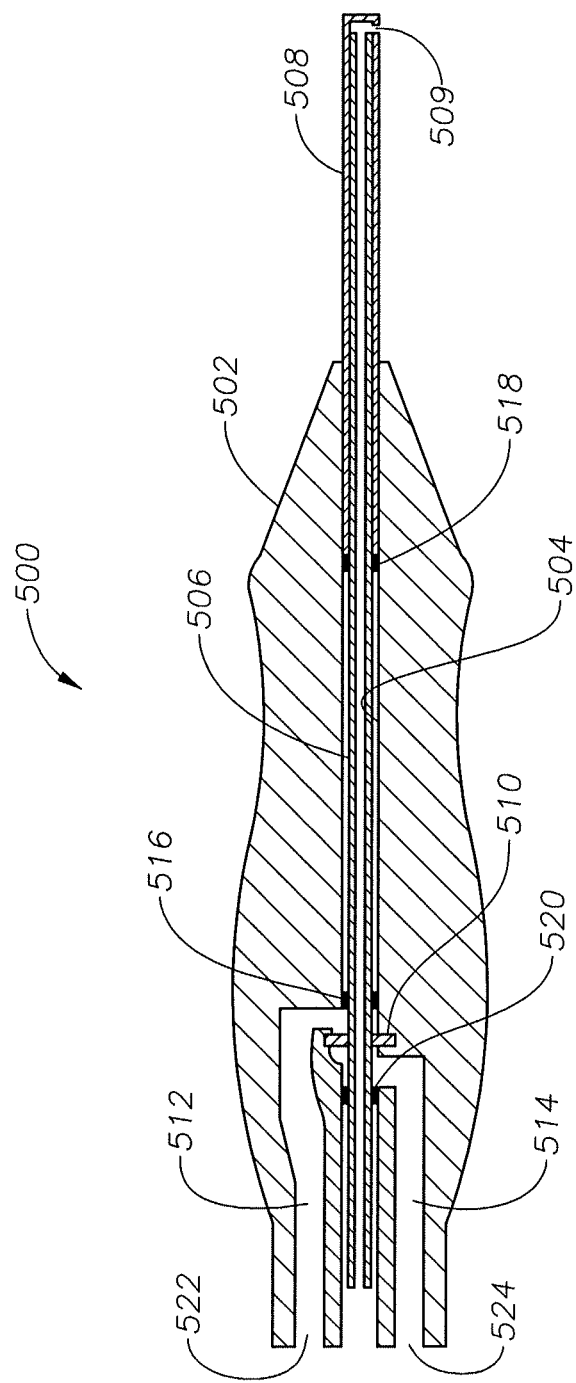
FIG. 5 is a cross-sectional view of an example dual-action hydraulic vitrectomy probe.

As indicated above, a dual-action vitrectomy probe is also within the scope of the disclosure. FIG. 5 shows a cross-sectional view of an example dual-action vitrectomy probe 500. The probe 500 may include a housing 502, a central passageway 504, a cutter 506 disposed in the central passageway 504 and operable to reciprocate therein. The cutter 506 may be hollow to allow aspiration of tissue, fluids, and other materials from the eye during operation of the probe 500. An outer sleeve 508 having a port 509 may be secured within the central passageway 504, and the cutter 506 may reciprocate within the outer sleeve 508, for example, in response to hydraulic pressure applied to diaphragm 510. The cutter 506 may be coupled to the diaphragm 510, and diaphragm 510 may be disposed between a first hydraulic chamber 512 and a second hydraulic chamber 514. Seals 516, 518, and 520 may also be included in the probe 500, and, in some instances, the seals 516, 518 and 520 may be fluid-tight. The probe 500 may also include a first port 522 in fluid communication with the first hydraulic chamber 512 and a second port 524 in fluid communication with the second hydraulic chamber 514. Thus, the first port 522 may be coupled to a first hydraulic line to supply hydraulic pressure to the first hydraulic chamber 512, and the second port 524 may be coupled to a second hydraulic line to supply hydraulic pressure to the second hydraulic chamber 512.

In operation, application of hydraulic pressure may be alternated between the first hydraulic chamber 512 and the second hydraulic chamber 514, thereby alternately applying hydraulic pressure to opposing sides of the diaphragm 510. As a result, the cutter 506 is made to reciprocate within the outer sleeve 508 to perform a cutting action. Tissue entering port 509 may be cut by the reciprocating cutter 506, and the tissue may be aspirated through the cutter 506. In other implementations, the diaphragms 320 and 510 may be replaced with a moveable piston. The moveable piston may be coupled to the cutter, such as cutter 309 and 506, to provide actuation of the cutter.

Figure 6:
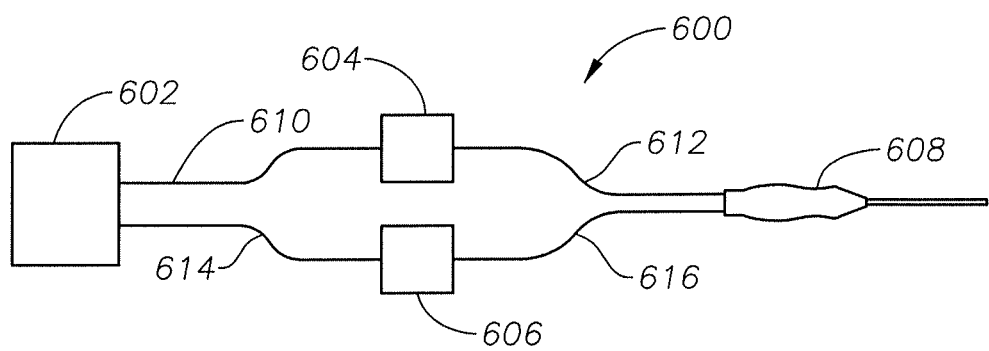
FIG. 6 is a schematic view of an example hydraulic vitrectomy probe system, such as for a dual-action hydraulic vitrectomy probe.

FIG. 6 shows another example hydraulic vitrectomy probe system 600 for a dual-action hydraulic vitrectomy probe. The system 600 may include a pneumatic system 602, a first pressure multiplier 604, a second pressure multiplier 606, and a hydraulic vitrectomy probe 608. The first pressure multiplier 604 may be coupled to the pneumatic system 602 via first pneumatic conduit 610 and to the probe 608 via a first hydraulic conduit 612. The second pressure multiplier 606 may be coupled to the pneumatic system 602 via a second pneumatic conduit 614 and to the probe 608 via a second hydraulic conduit 616. The first pressure multiplier 604 and the second pressure multiplier 606 may operate similar to the pressure multipliers 200 and/or 404, described above. Further, in some implementations, the first and second pressure multipliers 604 and 606 may be the same. That is, in some cases, the first and second pressure multipliers 604 and 606 may provide the same pressure increases. In other instances, the first and second pressure multipliers 604 and 606 may be different, so as to produce different pressure increases.

In operation, pneumatic pressure may be alternately applied to the first and second pressure multipliers 604 and 606. Consequently, hydraulic pressure is alternately applied to opposing sides a pressure-responsive mechanism, such as a diaphragm, to cause the cutter of the probe 608 to reciprocate.

In some instances, one or more of pressure multipliers 604 and 606 may be incorporated into the pneumatic system 602. In other instances, one or more of pressure multipliers 604 and 606 may be coupled directly coupled directly to the pressure system 602. In still other instances, one or more pressure multipliers utilized in a vitrectomy probe system may be integrated into a hydraulic vitrectomy probe. It may be desirable to have a pressure multiplier coupled as close as possible to the pneumatic system, to reduce a total pneumatic reservoir and, as such, increase a response time of the vitrectomy probe.

Hydraulic vitrectomy probes may have an adjustable port size (e.g., a port in which the maximum open size of the port may be adjustable during operation of the vitrectomy probe). For example, in some implementations, vitrectomy probes 300 and/or 500 may have a port size that may be adjusted during operation. For example, the size of ports 308 and 509 of probes 300 and 500, respectively, may be varied by adjusting a fully retracted position the cutters 309 and 506, respectively. Thus, the smaller amount by which the cutters 309 and 506 are retracted, the smaller the resulting port size opening.

In some instances, probes 300 and/or 500 may be coupled to a console, such as console 100. A surgeon may adjust the opening size of the port 308, 509 of probes 300 and 500, respectively, by manipulating a control of a console such as by manipulating the footswitch, such as footswitch 108. For example, the footswitch may include a pedal pivotable within a range, and the surgeon may adjust the size of the ports by actuating the pedal within the range. The footswitch may also include other controls, such as one or more buttons, for example, to adjust a cutting rate (e.g., the rate at which the probe's cutter is reciprocated), an aspiration rate (e.g., an amount of suction applied through the probe), and a duty cycle (e.g., a duration of the "off time" of the cutter when operation of the probe is selected to pulse). A duty cycle may be adjusted to "pulse" the probe. That is, that the cutter may be adjusted to oscillate at a certain frequency interrupted by pauses at a designated interval for a designated time period.

While some implementations may be primed remote in time and/or location from the time and/or place of manufacturing, in other implementations, one or more of a pressure multiplier or a hydraulic vitrectomy probe may be sterilized and primed at the time of manufacturing and may be shipped ready to use. For example, a pressure multiplier and/or hydraulic vitrectomy probe may be primed at the time of manufacturing with BSS®.

It should be understood that, although many aspects have been described herein, some implementations may include all of the features, others may include some features while including other, different features, and in still other instances, other implementations may omit some features while including others. That is, various implementations may include one, some, or all of the features described herein.

A number of implementations have been described. Nevertheless, it will be understood that various modifications may be made without departing from the spirit and scope of the disclosure. Accordingly, other implementations are within the scope of the following claims.

What is claimed is:

1. A hydraulic vitrectomy probe system comprising:
    a pneumatic pressure source adapted to repeatedly cycle application of a pressurized gas;
    a hydraulically actuated vitrectomy probe; and
    a pressure multiplier coupled at a first portion to the pneumatic pressure source and at a second portion to the hydraulically actuated vitrectomy probe and adapted to convert a pneumatic pressure received from the pneumatic pressure source into a hydraulic pressure output to the hydraulically actuated vitrectomy probe, the pressure multiplier comprising:
        a first chamber;
        a first diaphragm housed in the first chamber;
        a second chamber;
        a second diaphragm housed in the second chamber, the first diaphragm and the second diaphragm coupled to each other.

2. The hydraulic vitrectomy probe system of claim 1, wherein the first chamber of the pressure multiplier is fluidly coupled to the pneumatic pressure source and wherein the second chamber of the pressure multiplier is fluidly coupled to the hydraulically actuated vitrectomy probe.

3. The hydraulic vitrectomy probe system of claim 1, wherein the pressure multiplier is coupled to the pneumatic pressure source via a conduit.

4. The hydraulic vitrectomy probe system of claim 3, wherein the conduit is flexible tubing.

5. The hydraulic vitrectomy probe system of claim 1, wherein the pressure multiplier is directly coupled to the pneumatic pressure source.

6. The hydraulic vitrectomy probe system of claim 1, wherein the pressure multiplier is integrated into the pneumatic pressure source.

7. The hydraulic vitrectomy probe system of claim 1, wherein the pneumatic pressure source forms a part of an ophthalmic surgical console.

8. The hydraulic vitrectomy probe system of claim 1, wherein a surface area of the first diaphragm in contact with a pressurized gas supplied by the pneumatic pressure source is larger than a surface area of the second diaphragm in contact with a hydraulic fluid.

9. The hydraulic vitrectomy probe system of claim 1, wherein the hydraulic vitrectomy probe is coupled to the pressure multiplier via a conduit.

10. The hydraulic vitrectomy probe system of claim 9, wherein the conduit is flexible tubing.

11. The hydraulic vitrectomy probe system of claim 1, wherein the hydraulic vitrectomy probe is a single-action hydraulic vitrectomy probe.

12. The hydraulic vitrectomy probe system of claim 1, wherein the hydraulic vitrectomy probe is a dual-action probe.

13. The hydraulic vitrectomy probe system of claim 12, wherein the pressure multiplier is a first pressure multiplier, the hydraulic vitrectomy probe system further comprising a second pressure multiplier fluidly coupled to the pneumatic pressure source at a first portion of the second pressure multiplier and the hydraulic vitrectomy probe at a second portion of the second pressure multiplier, wherein the first pressure multiplier is adapted to supply hydraulic pressure to the hydraulic vitrectomy probe to actuate a cutter of the hydraulically actuated vitrectomy probe in a first direction, and wherein the second pressure multiplier is adapted to supply hydraulic pressure to the hydraulic vitrectomy probe to actuate the cutter of the hydraulically actuated vitrectomy probe in a second direction, opposite the first direction.

14. A method of operating a hydraulically actuated vitrectomy probe, the method comprising:
    applying a pneumatic pressure from a pneumatic pressure source to a pressure multiplier;
    converting the pneumatic pressure into a hydraulic pressure with the pressure multiplier; and
    actuating a cutter of the vitrectomy probe with the hydraulic pressure supplied from the pressure multiplier to the hydraulically actuated vitrectomy.

15. The method of claim 14, wherein applying a pneumatic pressure from a pneumatic pressure source to a pressure multiplier comprises supplying a pulsed pneumatic pressure to the pressure multiplier.

16. The method of claim 14, wherein applying a pneumatic pressure from a pneumatic pressure source to a pressure multiplier comprises applying the pneumatic pressure from the pneumatic pressure source that forms a part of an ophthalmic surgical console.

17. The method of claim 14, wherein converting the pneumatic pressure into a hydraulic pressure with the pressure multiplier comprises:
    receiving the pneumatic pressure into a pneumatic portion of the pressure multiplier against a first diaphragm contained within the pneumatic portion and in fluid contact with a gas transmitting the pneumatic pressure, the first diaphragm coupled to a second diaphragm disposed in a hydraulic portion of the pressure multiplier;
    displacing the first diaphragm and the second diaphragm with the pneumatic pressure; and
    displacing hydraulic fluid in contact with the second diaphragm to form the hydraulic pressure.

18. The method of claim 17, wherein displacing the first diaphragm and the second diaphragm with the pneumatic pressure comprises displacing the first diaphragm having a surface area in contact with the gas larger than a surface area of the second diaphragm in contact with the hydraulic fluid.

19. The method of claim 14, wherein actuating a cutter of the vitrectomy probe with the hydraulic pressure supplied from the pressure multiplier to the hydraulically actuated vitrectomy comprises cycling the cutter of the vitrectomy probe at a rate in the range of one to 20,000 cycles per minute.

20. A hydraulic vitrectomy probe system comprising:
    a pneumatic pressure source adapted to produce a pulsed pneumatic pressure by repeatedly cycling application of a pressurized gas;
    a hydraulic vitrectomy probe adapted to receive a pulsed hydraulic pressure; and
    a pressure multiplier in fluid communication with the pneumatic pressure source and adapted to receive the pulsed pneumatic pressure and in fluid communication with the hydraulic vitrectomy probe and adapted to transmit the pulsed hydraulic pressure to the hydraulic vitrectomy probe, the pressure multiplier comprising:
        a housing;
        a first chamber defined by a first portion of the housing;
        a second chamber defined by a second portion of the housing;
        a first diaphragm disposed in the first chamber, the first diaphragm having a surface in contact with the pressurized gas; and
        a second diaphragm disposed in the second chamber, the second diaphragm having a surface in contact with hydraulic fluid used to transmit the pulsed hydraulic pressure to the hydraulic vitrectomy probe, the first diaphragm coupled to the second diaphragm to form an operational assembly, the operational assembly adapted to convert the received pulsed pneumatic pressure into the pulsed hydraulic pressure.

21. The hydraulic vitrectomy probe system of claim 20, wherein the first diaphragm and the second diaphragm comprise retaining features formed along peripheral edges thereof, and wherein the retaining features are received into respective recesses formed in the housing.

22. The hydraulic vitrectomy probe system of claim 20, wherein the operational assembly further comprises a spacer disposed between the first diaphragm and the second diaphragm, the spacer adapted to transmit a movement of one of the first diaphragm or the second diaphragm to the other of the first diaphragm or the second diaphragm.

23. The hydraulic vitrectomy probe system of claim 20, wherein a surface area of the first diaphragm in contact with the pressurized gas is larger than an area of the second diaphragm in contact with the hydraulic fluid.

24. The hydraulic vitrectomy probe system of claim 20, wherein the pneumatic pressure source is fluidly coupled to the pressure multiplier by flexible tubing.

25. The hydraulic vitrectomy probe system of claim 20, wherein the hydraulic vitrectomy probe is fluidly coupled to the pressure multiplier by flexible tubing.

26. The hydraulic vitrectomy probe system of claim 20, wherein the pressure multiplier is directly coupled to the pneumatic pressure source.

* * * * *